(12) United States Patent
Styrc

(10) Patent No.: US 8,974,510 B2
(45) Date of Patent: Mar. 10, 2015

(54) TREATMENT DEVICE FOR A BLOOD CIRCULATION VESSEL

(75) Inventor: Mikolaj Witold Styrc, Kopstal (LU)

(73) Assignee: Laboratoires Perouse, Ivry Le Temple (FR)

( * ) Notice: Subject to any disclaimer, the term of this patent is extended or adjusted under 35 U.S.C. 154(b) by 470 days.

(21) Appl. No.: 12/816,640

(22) Filed: Jun. 16, 2010

(65) Prior Publication Data

US 2010/0324655 A1 Dec. 23, 2010

(30) Foreign Application Priority Data

Jun. 17, 2009 (FR) ...................................... 09 54074

(51) Int. Cl.
*A61F 2/06* (2013.01)
*A61F 2/962* (2013.01)
*A61F 2/95* (2013.01)

(52) U.S. Cl.
CPC ......... *A61F 2/962* (2013.01); *A61F 2002/9505* (2013.01); *A61F 2002/9511* (2013.01)
USPC ........................................ 623/1.11; 623/1.12

(58) Field of Classification Search
CPC ........ A61F 2/95; A61F 2/9505; A61F 2/9511
USPC ................ 623/1.11, 1.12, 1.23; 606/198, 194
See application file for complete search history.

(56) References Cited

U.S. PATENT DOCUMENTS

| 5,242,452 A | 9/1993 | Inoue |
| 5,676,696 A * | 10/1997 | Marcade ...................... 623/1.35 |
| 2004/0092845 A1 | 5/2004 | Gaber |
| 2010/0125322 A1 * | 5/2010 | Fitzgerald et al. ........... 623/1.11 |
| 2010/0268201 A1 * | 10/2010 | Tieu et al. .......................... 606/1 |

FOREIGN PATENT DOCUMENTS

WO 01/51114 A2 7/2001

OTHER PUBLICATIONS

French Search Report in Corresponding Application No. FA 723836/FR 0954074 Dated Feb. 3, 2010.

* cited by examiner

*Primary Examiner* — Katrina Stransky
(74) *Attorney, Agent, or Firm* — Young & Thompson

(57) ABSTRACT

The device includes at least a tubular endoprosthesis (6), deployable between a retracted state and a dilated state, and a hollow support (10) which extends longitudinally between a proximal end (18) and a distal end (16). The support (10) is provided, in the vicinity of the distal end (16), with at least a transverse retention opening. The device includes at least a releasable threadlike tie (12, 14) for holding the endoprosthesis (6) on the support (10). The tie is engaged in the retention opening (28) and actuated from the proximal end (18) of the support (10) to release the endoprosthesis (6). The support (10) includes, over at least a portion of its length, a spring (24) forming the support. The spring (24) has contiguous turns over at least a portion of its length.

13 Claims, 4 Drawing Sheets

TREATMENT DEVICE FOR A BLOOD CIRCULATION VESSEL

BACKGROUND OF THE INVENTION

Field of the Invention

The present invention relates to a treatment device for a blood circulation vessel of the type comprising:

at least a tubular endoprosthesis, deployable between a retracted state and a dilated state;

a hollow support which extends longitudinally between a proximal end and a distal end, said support being provided, in the vicinity of the distal end, with at least a transverse retention opening;

at least a releasable threadlike tie for holding the endoprosthesis on the support, the threadlike tie being engaged in the retention opening and actuated from the proximal end of the support to release the endoprosthesis.

DESCRIPTION OF THE RELATED ART

Document FR-A-2 863 160 describes a treatment device for a blood circulation vessel comprising an auto-expandable tubular endoprosthesis and a support for holding the endoprosthesis in a retracted state for insertion into the blood circulation vessel. Once the support has been inserted as far as the implantation site, the endoprosthesis is released and the support withdrawn.

Moreover the support and the endoprosthesis are surrounded by an insertion sheath facilitating forward movement in the blood circulation vessel.

To push the support axially in the blood network from its proximal end, it must have some rigidity.

However, this rigidity may prove somewhat impractical, particularly when passing the support through curved portions of blood circulation vessels, such as the aortic cross. It is therefore desirable for the device to be flexible.

BRIEF SUMMARY OF THE INVENTION

An object of the invention is therefore to provide a treatment device for a blood circulation vessel which is easy to insert and move forward in the blood network and which can nevertheless pass easily through curved portions.

The invention therefore relates to a device of the abovementioned type, characterised in that the support comprises, over at least a portion of its length, a spring forming the support, the spring having contiguous turns over at least a portion of its length.

According to particular embodiments, the device comprises one or more of the following features, taken in isolation or in any technically possible combinations:

the spring delimits a cylindrical inner wall and/or a cylindrical outer wall of the support;

two adjacent turns of the spring delimit between them the retention opening;

the support comprises at least a sleeve which is more rigid axially than the spring, the sleeve surrounding the spring opposite the retention opening;

the sleeve delimits a transverse opening for the passage of the threadlike tie, the passage opening extending opposite the retention opening;

at least one of the two adjacent turns extends opposite the passage opening so as to avoid contact of the threadlike tie with the contour of the passage opening when the threadlike tie is under tension;

the sleeve extends longitudinally between a distal end and a proximal end, at least one of the distal end and the proximal end being engaged with contiguous turns of the spring to immobilise the sleeve relative to the spring;

the treatment device comprises a tip for guiding the distal end of the support in the circulation vessel, the guide tip being fixed on the distal end of the support;

the guide tip is threaded on the spring of the support by engagement with the turns of the spring;

the guide tip comprises a flexible distal head and a rigid proximal shank, the proximal shank forming a spiral suitable for threading onto the spring; and the guide tip comprises a flexible proximal skirt;

The invention also relates to a system for placing an endoprosthesis in a blood circulation vessel, characterised in that it comprises a device as defined above and a sheath for inserting the device into the blood circulation vessel, the sheath surrounding the support and the endoprosthesis and comprising a capsule for placing the endoprosthesis which contains the endoprosthesis, the sheath being moveable axially along the support towards the proximal end to release the endoprosthesis from the sheath.

According to a particular embodiment of the placement system as defined above, the sheath comprises, over at least a portion of its length, a tubular spring with contiguous turns.

BRIEF DESCRIPTION OF THE DRAWINGS

The invention will be better understood on reading the description below, given purely by way of example and with reference to the accompanying drawings in which.

DETAILED DESCRIPTION OF THE PREFERRED EMBODIMENTS

Figure 1:
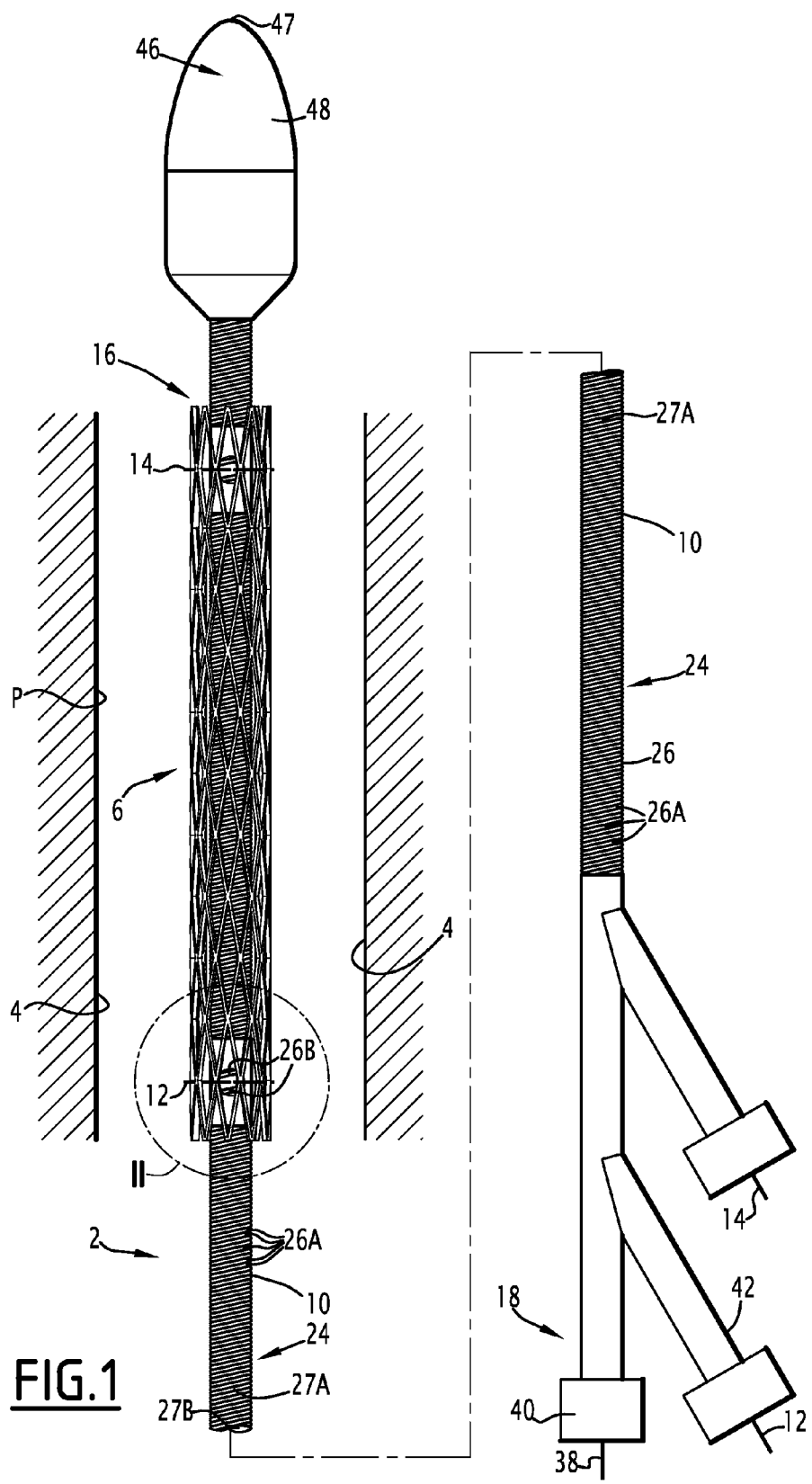
FIG. 1 is a diagrammatic view of a treatment device according to the invention in which only the distal and proximal portions of the system have been illustrated and in which, for greater clarity, the insertion sheath is not shown.

FIG. 1 shows a treatment device 2 for a blood circulation vessel 4.

The device 2 is suitable for the insertion and placement of an implant consisting of a tubular endoprosthesis 6 in an implantation site P of the blood circulation vessel 4.

In a variant, the implant is an endoprosthesis 6 carrying an obturation valve placed in an inner blood circulation passage defined by the endoprosthesis. The implant in this case is an endovalve.

The tubular endoprosthesis 6 is auto-expandable, in other words it can be deployed spontaneously from a retracted state in which it has a small diameter to a dilated state in which it has a larger diameter, the dilated state being the rest state.

The device 2 also comprises a hollow support 10 on which the endoprosthesis 6 is mounted coaxially and releasable ties 12, 14 for holding the endoprosthesis 6 on the support 10 in the retracted state.

The support 10 extends longitudinally between a distal end 16 and a proximal end 18.

The endoprosthesis 6 is arranged in the support 10, in the vicinity of the distal end 16 thereof.

The distal end 16 is designed to be implanted in the blood circulation vessel 4 while the proximal end 18 is designed to remain accessible to the surgeon outside the patient's body.

The support 10 according to the invention has the feature of consisting, over a portion of its length, of a spring 24 with turns 26. Over substantially the entire length of the spring 24, the turns 26 are contiguous turns 26A. Thus over at least a portion of its length, the spring 24 has contiguous turns 26A.

The spring 24 is deformable by bending in the region of each turn 26A between a rest state in which the turns 26A are in contact with one another and a state deformed by bending in which at least one of the contiguous turns 26A of the spring 24 is separated from the adjacent turns.

Thus, a spring with contiguous turns is taken to mean a spring of which the turns, in the rest state of the spring, are in contact with one another over the entire circumference of the turns. A spring with contiguous turns defines a continuous tubular wall over the portion of the spring in which the turns are contiguous and in the rest state.

Figure 2:
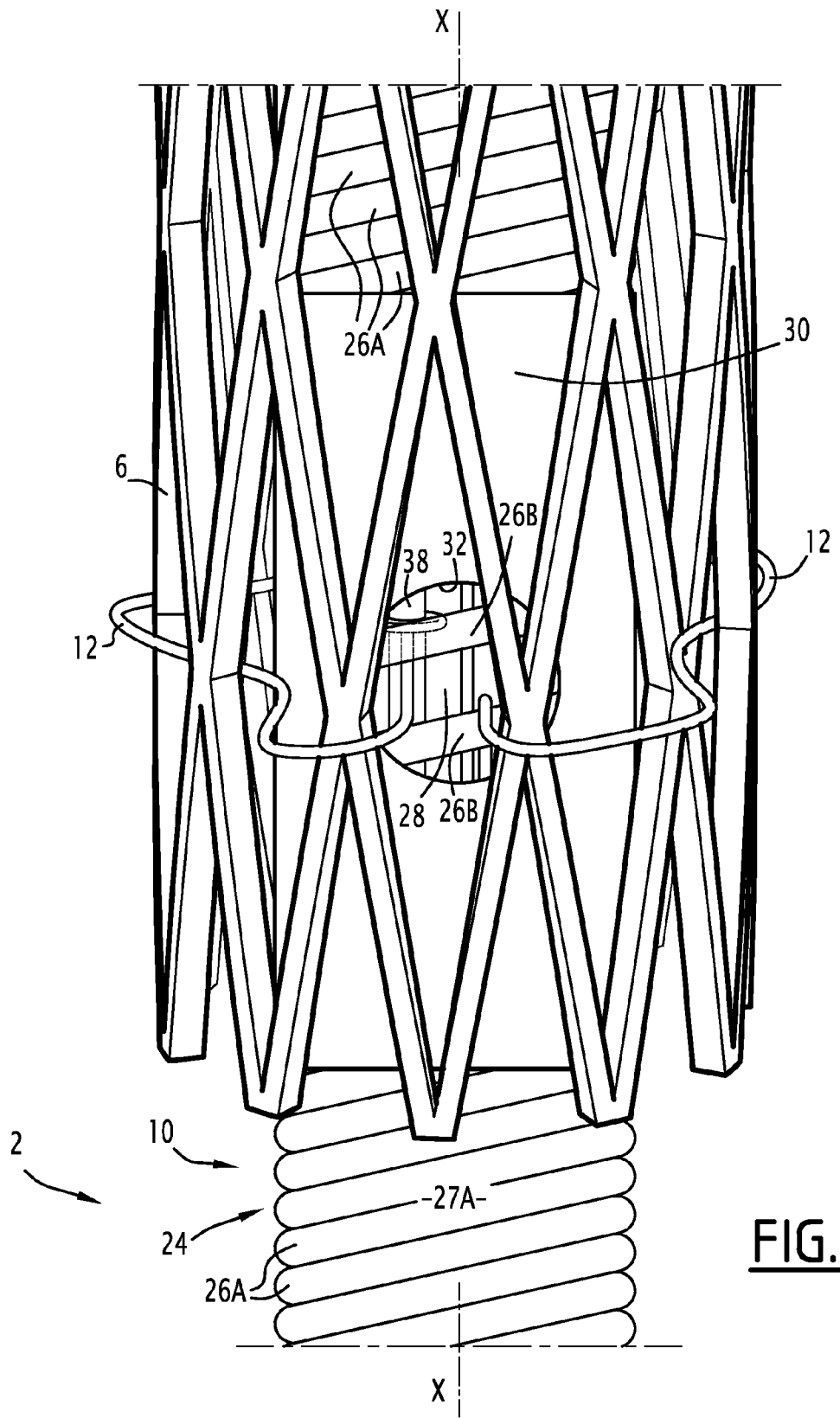
FIG. 2 is an enlarged view of a detail marked II in FIG. 1.

The spring 24 therefore forms the outer wall 27A and the inner wall 27B of the support 10 (see FIGS. 1 and 2). The support 10 therefore consists, over at least a portion of its length, of all or part of the spring 24.

The walls 27A, 27B delimit a generally continuous surface and extend axially.

The spring 24 illustrated is a cylindrical helix. The spring 24 has a circular cross-section but in a variant may have a non-circular cross-section. Generally, the spring 24 is tubular.

The cross-section of the turns 26 is of any suitable type, for example circular.

The spring 24 extends over the entire distal end portion of the support 10, in other words over the portion of the support 10 designed to be inserted into the patient's body. In a variant, the spring 24 extends over any suitable length of the support 10.

In the rest state, the support 10 extends axially.

In the deformed state, the support 10 bends laterally relative to the support 10 in the rest state.

The spring 24 has symmetry of revolution providing uniform flexibility in any direction transverse to the support 10.

However, in a variant, the spring 24 is arranged so as to deform under bending in a preferred direction, the turns of the spring 24 for example being bound by a coating whilst on the opposite generatrix the turns of the spring are free along a generatrix parallel to the axis of the spring. The coating is made of polytetrafluoroethylene (PTFE), for example.

For the passage of the ties 12 and 14, the spring 24 also has two zones in which at least two adjacent turns 26B are spaced, in the rest state of the spring, to delimit between them an opening 28 known as the retention opening through which the corresponding tie 12, 14 is engaged (see FIG. 2).

The support 10 is provided with a sleeve 30 arranged opposite each opening 28 to provide axial rigidity for the support 10, specifically rigidity in compression and in traction along the longitudinal axis X-X of the support 10.

Each sleeve 30 surrounds the spring 24 and delimits an opening 32 for the passage of the corresponding tie 12, 14. The passage opening 32 extends opposite the retention opening 28.

At least two adjacent spaced turns 26B extend opposite the opening 32 of the corresponding sleeve 30.

The tie 14 passes between the two adjacent spaced turns 26B. The tie 14 is therefore guided by the turns 26B to the passage opening 32. Once under tension, the corresponding tie 12, 14 therefore slides against the surface of the turns 26B and not against the contour of the passage opening 32 of the sleeve 30. Improved sliding of the ties 12, 14 is thereby achieved.

The sleeve 30 is fixed on the spring 24 by engagement of the distal and proximal ends thereof with the contiguous turns 26A of the spring 24.

The sleeve 30 is therefore provided with a radial lip for example, engaging with the contiguous turns 26A.

The ties 12, 14 each form a loop passing round the endoprosthesis 6 or, as illustrated in FIG. 2, alternately inside and outside the mesh of the endoprosthesis 6.

The free end of the tie 12, 14 is held for example by a rod 38 of which the proximal end is actuated in the region of a proximal branch 40 of the support 10, while the proximal end of the corresponding tie 12 can be actuated in the region of another proximal branch 42 of the support 10. Reference may be made for example to application FR-A-2 863 160 for an example of an arrangement of the retention means of the endoprosthesis 6.

Generally, any retention tie may be used for the endoprosthesis 6. It may for example be a tie of which both free ends can be actuated from the proximal end 18 of the support 10.

The spring 24 is made of any suitable type of material. The stiffness of the spring 24 is suitable for providing sufficient axial rigidity under traction. The stiffness can be adjusted by the tension of the lasso.

The spring 24 has a diameter of between 2 mm and 10 mm, for example.

The turns 26 have a diameter of between 0.2 mm and 1.5 mm, for example.

Figure 3:
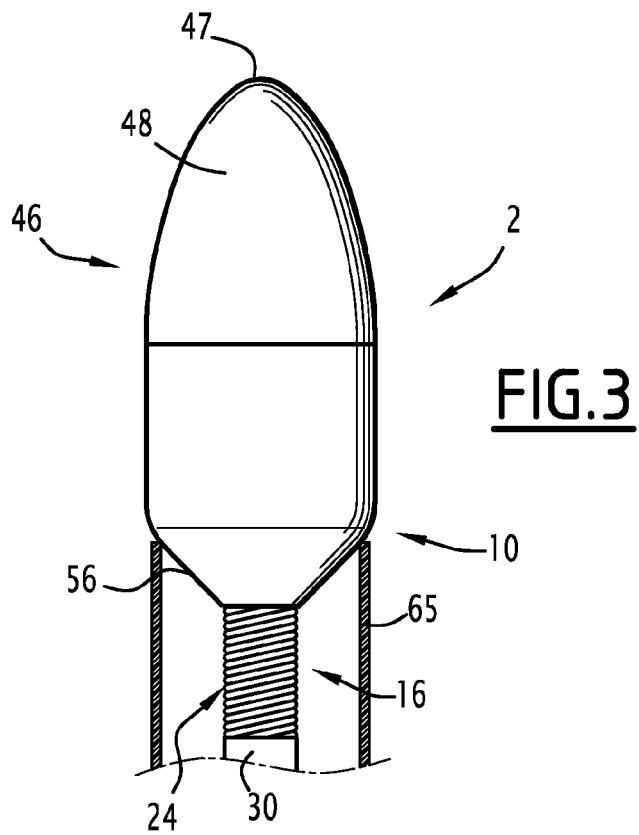
FIG. 3 is an enlarged view of the distal end of the device of FIG. 1, in which, for greater clarity, the endoprosthesis is not shown, FIG. 3 illustrating more particularly the distal end of the device consisting of a guide tip.
Figure 5:
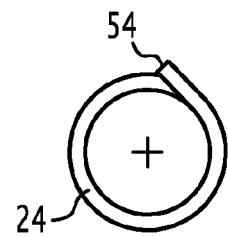
FIG. 5 is a front view of the distal end of the support receiving the guide tip.
Figure 4:
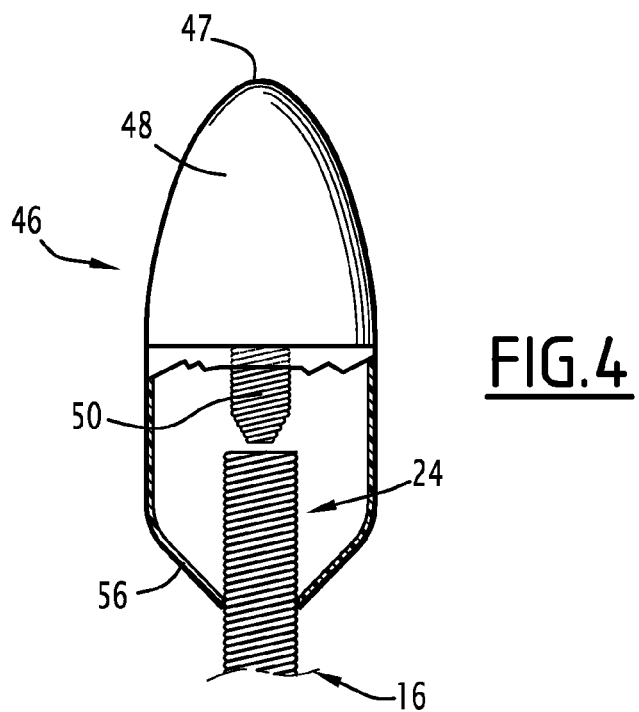
FIG. 4 is a similar view to that of FIG. 3 of the guide tip of FIG. 3 shown on its own.

FIGS. 3 to 5 illustrate the device 2 more particularly in the region of the distal end 16 of the support 10.

As well as the support 10, the device 2 comprises a guide tip 46 forming the distal end 47 of the device 2.

The guide tip 46 is suitable for providing atraumatic contact with the blood circulation vessel 4 and accordingly comprises a flexible head 48 which is streamlined when moving distally. The head 48 is in the form of an ogive, for example.

The guide tip 46 is also provided to guide the distal end 16 of the support 10. It therefore has a very short proximal shank 50 (FIG. 4) fixed on the support 10.

In the example shown, the proximal shank 50 is flexible. The shank 50 is spiral shaped so that it can be threaded inside the spring 24.

The spring 24 also has a limit stop 54 to prevent the guide tip 46 (see FIG. 5) from unscrewing at the end of the threading travel.

The limit stop 54 is formed by the free end of the turns 26 of the spring 24. The free end thus forms a radially projecting rectilinear portion.

As can be seen in FIGS. 3 and 4, the guide tip 46 also comprises a resilient skirt 56 surrounding the shank 50 and the distal end of the spring 24 and extending the head 48 towards the proximal end of the tip 46. The skirt 56 therefore has an outer surface contiguous with the edge of the surface of the head 48 and with the outer surface of the spring 24. The skirt 56 thus facilitates the atraumatic sliding of the device 2 against the blood circulation vessel 4 during insertion and withdrawal of the device 2.

Figure 6:
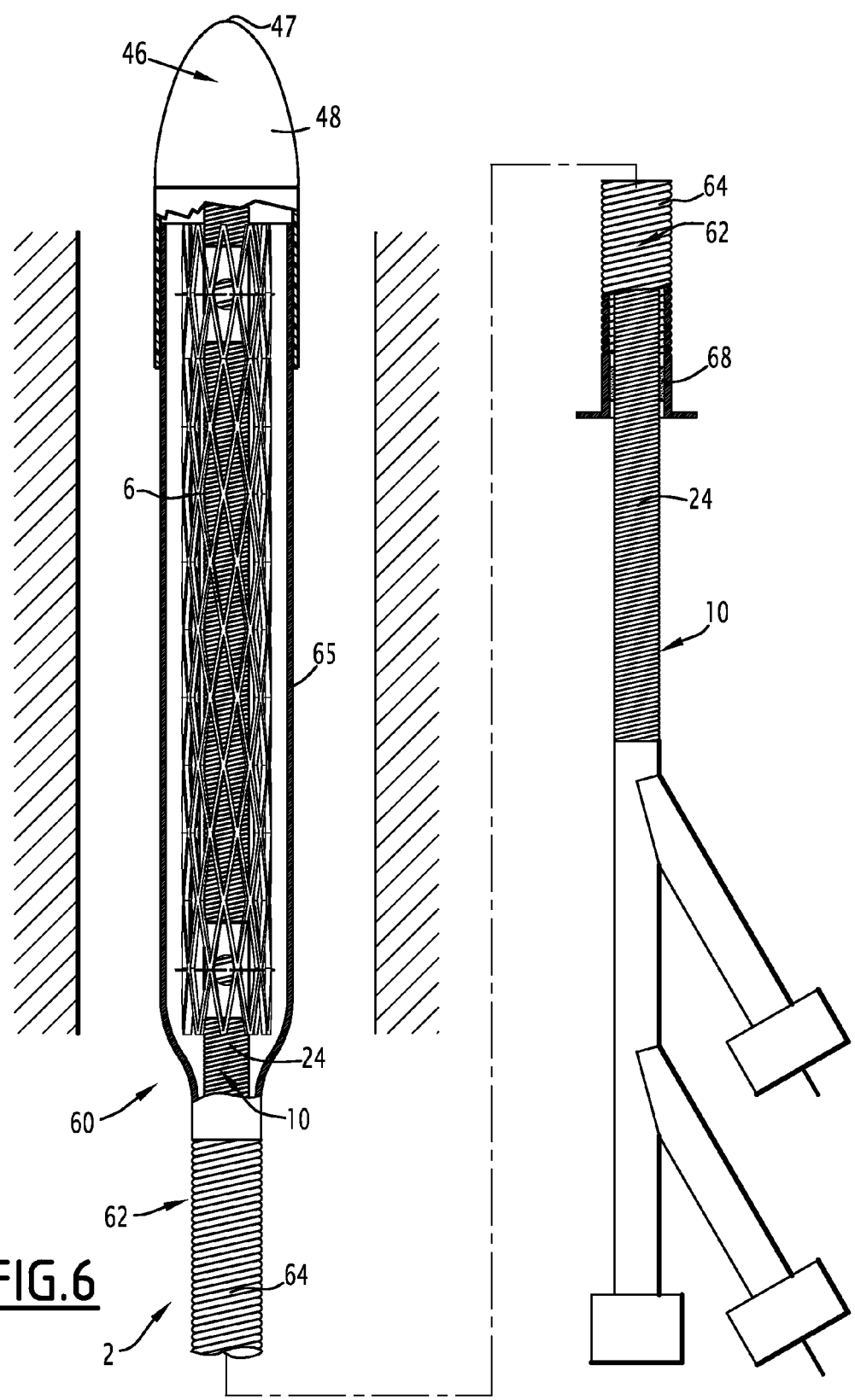
FIG. 6 is a view similar to FIG. 1 also showing the insertion sheath surrounding the device.

FIG. 6 shows a placement system 60 comprising the treatment device 2. The system 60 also comprises an insertion sheath 62 designed to prevent any significant reflux of blood towards the proximal end of the device 2 and facilitate the insertion and withdrawal of the device 2.

The sheath 62 surrounds the distal portion of the treatment device 2, with the exception of the head 48 and the guide tip 46.

The sheath 62 according to the invention also has the feature of consisting, over at least a portion of its length, of a spring 64 with contiguous turns of the same type as the spring 24 of the support 10.

The sheath 62 comprises a placement capsule 65 and the spring 64.

The capsule 65 surrounds the support 10 in the region of the endoprosthesis 6.

The capsule 65 is arranged at the distal end of the spring 64.

In the example illustrated, the resilient skirt 56 of the guide tip rests on the circumference of the distal end of the capsule 65. The skirt 56 therefore protects the blood circulation vessel 4 from penetrative contact by the distal end of the capsule 65.

The skirt 56 can therefore move spontaneously between a radially expanded configuration, seen in FIG. 6, in which it is applied externally round the capsule 65 and a radially retracted configuration towards the shank 50 constituting the rest configuration.

The placement capsule 65 is of any type suitable for being withdrawn before deployment of the endoprosthesis 6. In the example shown, it is moved towards the proximal end 18. After the endoprosthesis has been moved, the capsule is slid back against the guide tip 46, which corresponds to the position of the capsule 65 shown in FIG. 3. In a variant, the capsule 65 comprises means for tearing the capsule 65 longitudinally to completely release the endoprosthesis 6.

It should be noted that in the region of its proximal end the sheath 62 also comprises a sealing component 68 to provide sealing against blood around the support 10. It may be made of foam, for example.

An example of the operation of the placement system 60 provided with a treatment device 2 according to the invention is described below.

Initially, the system 60 is kept in its packaging (not shown), with the endoprosthesis 6 in the rest state.

Next, the surgeon removes the system from its packaging. He implants a surgical guide (not illustrated) circulating in the blood circulation vessel 4 from the external insertion point to the implantation zone P in which the tubular endoprosthesis 6 is to be implanted.

Next the surgeon inserts the system 60 into the blood circulation vessel 4, along the guide thread.

In linear portions of the blood circulation vessel 4, the springs 24 and 64 of the support 10 and of the sheath 62 are in the rest state.

When the surgeon inserts the system 60 into a bend of the blood circulation vessel 4, the springs 24 and 64 move from the rest state to the state in which they are deformed by bending, thereby facilitating passage.

When the implantation zone P is reached, the surgeon withdraws the capsule 65, by moving the capsule 65 towards the proximal end 18 of the support 10, to expose the endoprosthesis 6.

The surgeon then releases the retaining threads 12 and 14 to deploy the endoprosthesis 6 to the dilated state.

In the dilated state, the endoprosthesis 6 rests against the blood circulation vessel 4.

The surgeon next withdraws the rod 38 and then the threads 12 and 14 through the proximal end of the support 10.

After deployment of the endoprosthesis 6, said endoprosthesis is in the dilated state.

The surgeon slides the capsule 65 against the skirt 56 towards the distal end of the support 10 inside the endoprosthesis (see FIG. 3).

Finally, the surgeon withdraws the system 60 from the patient's body. The treatment device 2, which comprises the support 10 and the tip 46, and the insertion sheath 62 are therefore withdrawn simultaneously. The guide tip 46 passes inside the endoprosthesis 6.

Because of the spring 24, the treatment device 2 according to the invention provides great flexibility about a transverse axis of the support 10. The result is that the stresses applied to the curved portions of the blood circulation vessel 4 are not as great and insertion is therefore atraumatic.

Moreover, because the spring 24 has contiguous turns, it has good rigidity in axial compression along its longitudinal axis which ensures good forward movement when the proximal end is pushed by the surgeon.

The skirt 56 provides a continuous contact surface with the vessel 4 between the outer surface of the head 48 of the guide tip 46 and the outer surface of the capsule 65.

The sleeves 30 reinforce the axial rigidity of the support in the region of the retention openings 28. In reality, the turns 26B of the spring 24 must be spaced in the region of the openings 28 for the passage of the retention ties 12, 14, and without the sleeves, the axial rigidity of the support 10 under traction and particularly in compression would be diminished.

Threading the tip 46 on the spring 24 makes it easier to assemble the device. This type of fixing is also reliable.

The skirt 56 of the guide tip 46 makes it easier to slide the device 2 against the blood circulation vessel 4 when inserting and withdrawing the device 2.

Because of the spring 64, the insertion sheath 62 has the same advantages of rigidity in axial compression and flexibility under bending as the support 10.

The invention claimed is:

1. A treatment device for a blood circulation vessel, comprising:
   at least one tubular endoprosthesis, deployable between a retracted state and a dilated state;
   a hollow support which extends longitudinally between a proximal end and a distal end, said support being provided, in the vicinity of the distal end, with at least a transverse retention opening; and
   at least one releasable threadlike tie for holding the endoprosthesis on the support, the threadlike tie being engaged in the retention opening and actuated from the proximal end of the support to release the endoprosthesis;
   wherein the support comprises, over at least a portion of its length, a spring forming the support, the spring having contiguous turns over at least a portion of its length, and the spring delimiting an inner cylindrical wall and/or an outer cylindrical wall of the support; and
   wherein two adjacent turns of the spring delimit between them the retention opening, the two adjacent turns belonging to the same spring, the threadlike tie being inserted from the outer cylindrical wall through the two adjacent turns of the spring and the retention opening formed by the two adjacent turns of the spring.

2. The treatment device according to claim 1, wherein the support comprises at least a sleeve which is more rigid axially than the spring, the sleeve surrounding the spring opposite the retention opening.

3. The treatment device according to claim 2, wherein the sleeve delimits a transverse opening for the passage of the threadlike tie, the passage opening extending opposite the retention opening.

4. The treatment device according to claim 3, wherein at least one of the two adjacent turns extends opposite the passage opening so as to avoid contact of the threadlike tie with the contour of the passage opening when the threadlike tie is under tension, and wherein the threadlike tie is guided by the turns to the passage opening.

5. The treatment device according to claim 3, wherein the sleeve extends longitudinally between a distal end and a proximal end, at least one of the distal end and the proximal end being engaged with the contiguous turns of the spring to immobilise the sleeve relative to the spring.

6. The treatment device according to claim 4, wherein the sleeve extends longitudinally between a distal end and a proximal end, at least one of the distal end and the proximal end being engaged with the contiguous turns of the spring to immobilise the sleeve relative to the spring.

7. The treatment device according to claim 1, comprising a guide tip for guiding the distal end of the support in the blood circulation vessel, the guide tip being fixed on the distal end of the support.

8. The treatment device according to claim 7, wherein the guide tip is threaded on the spring of the support by engagement with the turns of the spring.

9. The treatment device according to claim 8, in which the guide tip comprises a distal head and a proximal shank, the proximal shank forming a spiral suitable for threading onto the spring.

10. The treatment device according to claim 9, wherein the guide tip comprises a flexible proximal skirt.

11. The treatment device according to claim 8, in which the guide tip comprises a flexible proximal skirt.

12. A system for placing an endoprosthesis in a blood circulation vessel, the system comprising:

a device according to claim 1; and a sheath for inserting the device into the blood circulation vessel, the sheath surrounding the support and the endoprosthesis and comprising a capsule for placing the endoprosthesis which contains the endoprosthesis, the sheath being moveable axially along the support towards the proximal end to release the endoprosthesis from the sheath.

13. The placement system according to claim 12, wherein the sheath comprises, over at least a portion of its length, a tubular spring with contiguous turns.

* * * * *